United States Patent [19]

Yamamoto

[11] Patent Number: 5,236,906
[45] Date of Patent: Aug. 17, 1993

[54] TOPICAL THERAPEUTIC PREPARATION

[75] Inventor: Toshiko Yamamoto, Fujisawa, Japan

[73] Assignee: Takeda Chemical Industries, Ltd., Osaka, Japan

[21] Appl. No.: 635,500

[22] PCT Filed: Dec. 4, 1990

[86] PCT No.: PCT/JP90/01573
§ 371 Date: Jan. 3, 1991
§ 102(e) Date: Jan. 3, 1991

[87] PCT Pub. No.: WO91/07974
PCT Pub. Date: Jun. 13, 1991

[30] Foreign Application Priority Data
Dec. 5, 1989 [JP] Japan .................. 1-316766

[51] Int. Cl.$^5$ .............................. A61K 31/56
[52] U.S. Cl. .................... 514/171; 514/54; 514/174; 514/179; 514/459
[58] Field of Search .............. 514/54, 179, 171, 174, 514/459

[56] References Cited

U.S. PATENT DOCUMENTS 4,736,024  4/1988  Della Valle et al. .......... 536/55.3

FOREIGN PATENT DOCUMENTS 0224987  6/1987  European Pat. Off. .

*Primary Examiner*—Leonard Schenkman
*Attorney, Agent, or Firm*—Wegner, Cantor, Mueller & Player

[57] ABSTRACT

A topical therapeutic preparation which contains an adrenocortical hormone and hyaluronic acid, the amount of said adrenocortical hormone being lower than the usual clinical dose of it, is used for combatting a skin disease.

6 Claims, No Drawings

TOPICAL THERAPEUTIC PREPARATION

FIELD OF THE INVENTION

The present invention relates to a dermatological composition for external use and more particularly to a topical dermatological composition which insures therapeutic efficacy at a sub-usual concentration of adrenocortical hormone.

BACKGROUND OF THE INVENTION

Adrenocortical hormone exhibits excellent efficacy in many diseases of the skin such as eczema/dermatitis represented by acute or chronic eczema, contact dermatitis, atopic dermatitis, etc., prurigo, e.g. strophulus and urticaria, cutaneous pruritus, psoriasis, etc. and as such has been widely used in clinical practice.

While adrenocortical hormone has very useful pharmacologic efficacy as aforesaid, long-term use of this hormone causes systemic side effects such as suppression of pituitary adrenocortical function even if it is externally used, not to speak of local skin infections and skin symptoms such as acne characteristic of this hormone. Therefore, for securing safety, the hormone is preferably used at a concentration as low as possible. However, any therapy with a topical preparation containing this hormone at such a low concentration cannot insure a sufficient therapeutic effect in such refractory diseases. To enhance the percutaneous absorption of adrenocortical hormone, it has been proposed to use this hormone in a topical therapeutic system containing a percutaneous absorption promoting agent such as urea, propylene glycol, etc. Another approach to this goal is the use of a therapeutic tape which takes advantage of the so-called occlusive dressing technique (ODT), such as Drenison Tape (Dainippon Pharmaceutical Co., Ltd., Japan). However, many problems such as skin irritation, inconvenience in use and so on remain to be solved. Under the circumstances, the advent of a topical therapeutic preparation which would be safe and easy to use has been keenly awaited. The inventor of the present invention explored the possibility of insuring a sufficient therapeutic effect with a topical preparation containing a reduced concentration of adrenocortical hormone and found that when hyaluronic acid is incorporated in a topical therapeutic composition containing adrenocortical hormone in such a reduced concentration, a therapeutic effect comparable to or even surpassing the effect obtainable with the conventional topical preparation containing the usual clinical dose of this hormone can be obtained. The present invention is predicated on the above finding.

SUMMARY OF THE INVENTION

This invention provides a topical therapeutic composition containing adrenocortical hormone and hyaluronic acid, the amount of said adrenocortical hormone being lower than the usual clinical dose of adrenocortical hormone.

DETAILED DESCRIPTION OF THE INVENTION

The present invention provides a topical therapeutic composition containing adrenocortical hormone and hyaluronic acid, the amount of said adrenocortical hormone being lower than the usual clinical dose of adrenocortical hormone. The term 'adrenocortical' hormone, as used in this specification means any and all of, inter alia, prednisolone, methylprednisolone, methylprednisolone acetate, prednisolone valerate acetate, cortisone, cortisone acetate, cortisone butyrate, hydrocortisone, hydrocortisone acetate, hydrocortisone butyrate, hydrocortisone butyrate propionate, flumethasone pivalate, triamcinolone, triamcinolone acetonide, dexamethasone, dexamethasone acetate, dexamethasone valerate, dexamethasone propionate, fluocinolone, fluocinolone acetonide, betamethasone, betamethasone valerate, betamethasone dipropionate, becromethasone propionate, clobetasone butyrate, fludroxycortide, fluocinonide, flunisolide, amcinonide, difluprednate, diflucortolone valerate, diflorasone acetate, clobetasol propionate and so on. Preferred are prednisolone, methylprednisolone, hydrocortisone acetate, hydrocortisone butyrate, flumethasone pivalate, dexamethasone acetate, fluocinolone, betamethasone valerate, betamethasone dipropionate, clobetasone butyrate, difluprednate, diflorasone acetate and clobetasol propionate.

The term 'hyaluronic acid', is used herein to mean not only hyaluronic acid but also any of pharmaceutically acceptable salts, such as sodium salt, thereof, and the present invention can be carried into practice by using any of hyaluronic acid, a salt thereof and a mixture thereof.

By adding about 0.005 to 0.1% by weight of hyaluronic acid to an adrenocortical hormone-containing dermatological preparation for external use, the hormone requirements can be reduced to less than the usual clinical dose of this hormone, for example to about one-half to about one-tenth.

Taking hydrocortisone butyrate as an example, the usual hydrocortisone butyrate content of topical dermatological preparations is 0.1% by weight (Japanese Pharmacopeia XI). However, by adding 0.01% by weight of hyaluronic acid, the hydrocortisone butyrate content can be reduced to 0.03% by weight.

The topical dermatological composition of the present invention can be manufactured by mixing hyaluronic acid, adrenocortical hormone and optionally additional conventional excipients for pharmaceutical preparations for topical use according to the established pharmaceutical procedure applicable generally to dermatological preparations for external use.

The human diseases in which the topical dermatological composition of the present invention may be indicated are the diseases for which the conventional adrenocortical hormone preparations are indicated, thus including eczema/dermatitis such as hand eczema, progressive keratoderma tylodes palmaris, lichen simplex or Vidal's disease, atopic dermatitis and chilitis, psoriasis, prurigo, insect bite, lichen planus and pustulosis palmoplantaris, among others.

Since hyaluronic acid is not irritating or toxic, the topical dermatological composition of the invention can be used in the same manner as the conventional adrenocortical hormone preparation for external use.

The following test example illustrates the efficacy of the topical dermatological composition of the present invention.

TEST EXAMPLE

The following three samples were compared by the skin pallor patch test which is generally used in the assessment of the clinicopharmacological efficacy of topical dermatological preparations.

A cream containing 0.1%* of hydrocortisone butyrate (hydrophilic ointment base; sample 1)

A cream containing 0.03% of hydrocortisone butyrate (hydrophilic ointment base; sample 2)

A cream containing 0.03% of hydrocortisone butyrate and 0.01% of hyaluronic acid (hydrophilic ointment base; sample 3)

*) This concentration of hydrocortisone butyrate is usually adopted on clinical use.

(All percents are by weight)

Thus, each sample, 60 mg, was coated on a patch test adhesive tape (Torii & Co., Ltd., Japan) and applied to the back of a healthy male adult subject. After 4 hours, the adhesive tape was removed and the pallor of the skin at the application site was macroscopically examined and rated 0.5, 2 and 4 hours later. While the four-point rating schedule indicated in Table 1 was used, the interval between points was further divided and the test results were rated with weights given to the respective findings according to the degree of evenness of the pallor for added precision in this trial.

TABLE 1

| | |
|---|---|
| 0 | No pallor |
| 1.0 | Pallor with an obscure border |
| 2.0 | Pallor with a well-defined border |
| 3.0 | Overt pallor with a well-defined border |

The results of the above comparative test are shown in Table 2.

TABLE 2

| | Degree of pallor | | |
|---|---|---|---|
| Sample | After 30 min. | After 2 hr. | After 4 hr. |
| 1 | 1.5 | 2.0 | 1.8 |
| 2 | 1.0 | 1.0 | 1.0 |
| 3 | 1.8 | 1.8 | 1.8 |

It is apparent from Table 2 that while sample 2 had a definitely less paling effect than sample 1, sample 3 was comparable to sample 1 in the skin paling effect.

This fact is also supported by the following Test Examples 2–4.

TEST EXAMPLE 2

In a similar manner to that described in Test Example 1, the following samples, which were summarized in Table 3, were prepared.

TABLE 3

| | | Concentration of | |
|---|---|---|---|
| Sample | Adrenocortical Hormone (A.H.) | A.H. (%) | Hyaluronic acid (%) |
| 4 | Cortisone | 1.0 | — |
| 5 | Acetate | 0.5 | 0.01 |
| 6 | | 0.5 | — |
| 7 | Prednisolone | 0.5 | — |
| 8 | | 0.25 | 0.01 |
| 9 | | 0.25 | — |
| 10 | Hydrocortisone | 1.0 | — |
| 11 | Acetate | 0.5 | 0.01 |
| 12 | | 0.5 | — |
| 13 | Dexamethasone | 0.05 | — |
| 14 | | 0.025 | 0.01 |
| 15 | | 0.025 | — |

Thus each sample, 50 mg, was coated on a patch test adhesive tape (Torii & Co., Ltd., Japan) and applied to the back of a healthy male adult subject. After 6 hours, the adhesive tape was removed and the pallor of the skin at the application site was macroscopically examined and rated 0.5, 2 and 4 hours later. While the four-point rating schedule indicated in Table 1 in the Test Example 1 was used, the interval between points was futher divided and the test results were rated with weights given to the respective findings according to the degree of evenness of the pallor for added precision in this trial.

The results of the above comparative test are shown in Table 4.

TABLE 4

| | Degree of pallor | | |
|---|---|---|---|
| Sample | After 0.5 hr. | After 2 hr. | After 4 hr. |
| 4 | 1.0 | 1.0 | 1.0 |
| 5 | 1.0 | 1.8 | 1.5 |
| 6 | 0.8 | 1.0 | 1.0 |
| 7 | 2.0 | 2.0 | 1.0 |
| 8 | 2.0 | 2.0 | 1.5 |
| 9 | 1.0 | 1.0 | 1.0 |
| 10 | 2.0 | 2.0 | 1.0 |
| 11 | 2.0 | 2.0 | 1.5 |
| 12 | 1.5 | 1.5 | 1.0 |
| 13 | 2.0 | 3.0 | 1.0 |
| 14 | 2.0 | 2.5 | 2.0 |
| 15 | 1.0 | 2.0 | 1.2 |

TEST EXAMPLE 3

In a similar manner to that described in Test Example 1, the following samples, which were summarized in Table 5, were prepared.

TABLE 5

| | | Concentration of | |
|---|---|---|---|
| Sample | Adrenocortical Hormone (A.H.) | A.H. (%) | Hyaluronic acid (%) |
| 16 | Betamethasone | 0.12 | — |
| 17 | valerate | 0.06 | 0.01 |
| 18 | | 0.06 | — |
| 19 | Fluocinonide | 0.05 | — |
| 20 | | 0.015 | 0.01 |
| 21 | | 0.015 | — |
| 22 | | 0.005 | 0.01 |
| 23 | | 0.005 | — |
| 24 | Betamethasone | 0.064 | — |
| 25 | dipropionate | 0.02 | 0.01 |
| 26 | | 0.02 | — |
| 27 | | 0.0064 | 0.01 |
| 28 | | 0.0064 | — |
| 29 | Difluprednate | 0.05 | — |
| 30 | | 0.015 | 0.01 |
| 31 | | 0.015 | — |
| 32 | | 0.005 | 0.01 |
| 33 | | 0.005 | — |
| 34 | Clobetasol | 0.05 | — |
| 35 | propionate | 0.015 | 0.01 |
| 36 | | 0.015 | — |
| 37 | | 0.005 | 0.01 |
| 38 | | 0.005 | — |

Thus, each sample, 50 mg, was coated on a patch test adhesive tape (Torri & Co., Ltd., Japan) and applied to the back of a healthy male adult subject. After 4 hours, the adhesive tape was removed and the pallor of the skin at the application site was macroscopically examined and rated 0.5, 2 and 4 hours later. While the four-point rating schedule indicated in Table 1 in the Test Example 1 was used, the interval between points was further divided and the test results were rated with weights given to the respective findings according to the degree of evenness of the pallor for added precision in this trial.

The results of the above comparative test are shown in Table 6.

TABLE 6

| Sample | Degree of pallor | | |
|---|---|---|---|
| | After 0.5 hr. | After 2 hr. | After 4 hr. |
| 16 | 2.0 | 2.0 | 1.0 |
| 17 | 2.0 | 2.0 | 2.0 |
| 18 | 1.0 | 1.0 | 1.5 |
| 19 | 2.0 | 3.0 | 2.0 |
| 20 | 2.0 | 3.0 | 2.0 |
| 21 | 1.0 | 2.0 | 2.0 |
| 22 | 1.0 | 2.0 | 1.5 |
| 23 | 0.8 | 1.0 | 1.0 |
| 24 | 2.0 | 2.0 | 1.5 |
| 25 | 2.0 | 2.0 | 2.0 |
| 26 | 1.0 | 2.0 | 1.0 |
| 27 | 1.5 | 1.5 | 1.0 |
| 28 | 1.0 | 1.0 | 1.0 |
| 29 | 2.5 | 3.0 | 2.0 |
| 30 | 2.5 | 3.0 | 2.0 |
| 31 | 2.0 | 2.0 | 1.5 |
| 32 | 2.0 | 2.0 | 1.5 |
| 33 | 1.5 | 1.5 | 1.0 |
| 34 | 3.0 | 3.0 | 3.0 |
| 35 | 3.0 | 3.0 | 3.0 |
| 36 | 2.0 | 2.5 | 2.5 |
| 37 | 2.0 | 2.5 | 2.5 |
| 38 | 2.0 | 2.0 | 2.0 |

TEST EXAMPLE 4

In a similar manner to that described in Test Example 1, the following samples, which were summarized in Table 7, were prepared.

TABLE 7

| Sample | Adrenocortical Hormone (A.H.) | Concentration of | |
|---|---|---|---|
| | | A.H. (%) | Hyaluronic acid (%) |
| 39 | Hydrocortizone butyrate | 0.1 | — |
| 40 | | 0.03 | 0.1 |
| 41 | | 0.03 | 0.005 |
| 42 | | 0.03 | — |

Thus, each sample, 50 mg, was coated on a patch test adhesive tape (Torii & Co., Ltd., Japan) and applied to the back of a healthy male adult subject. After 4 hours, the adhesive tape was removed and the pallor of the skin at the application site was macroscopically examined and rated 0.5, 2 and 4 hours later. While the four-point rating schedule indicated in Table 1 in the Test Example 1 was used, the interval between points was further divided and the test results were rated with weights given to the respective findings according to the degree of evenness of the pallor for added precision in this trial.

The results of the above comparative test are shown in Table 8.

TABLE 8

| Sample | Degree of pallor | | |
|---|---|---|---|
| | After 0.5 hr. | After 2 hr. | After 4 hr. |
| 39 | 1.5 | 1.8 | 1.8 |
| 40 | 1.5 | 1.8 | 1.8 |
| 41 | 1.2 | 1.8 | 2.0 |
| 42 | 1.0 | 1.0 | 1.2 |

EXAMPLE

The following example is intended to illustrate the invention in further detail and should by no means be construed as defining the metes and bounds of the invention.

| Formula | Example | |
|---|---|---|
| a) White petrolatum | 250 | g |
| b) Stearyl alcohol | 200 | g |
| c) Glycerin monostearate | 10 | g |
| d) Polyoxyethylene hardened castor oil 60 | 40 | g |
| e) Propylene glycol | 120 | g |
| f) Methyl p-hydroxybenzoate | 1 | g |
| g) Propyl p-hydroxybenzoate | 1 | g |
| h) Hyaluronic acid | 0.1 | g |
| i) Hydrocortisone butyrate | 0.3 | g |
| j) Pure water | 377.6 | g |
| Total | 1000 | g |

A mixture of a) through d) is stirred at about 75° C. to give a homogenous fluid. To e) are added f) through j), if necessary followed by warming for dissolution, and the solution is diluted with j) and warmed to about 75° C. This solution is added to the above-mentioned homogenous fluid at about 75° C. and the mixture is stirred to give an emulsion. This emulsion is cooled and stirred well until it hardens to give a cream.

When three patients with contact dermatitis were treated with the cream prepared as above, symptoms of dermatitis disappeared in all of them within 3 to 7 days.

What we claim is:

1. A topical dermatological composition consisting essentially of
   (a) an adrenocortical hormone selected from the group consisting of
      prednisolone, methylprednisolone, methylprednisolone acetate, prednisolone valerate acetate, cortisone, cortisone acetate, cortisone butyrate, hydrocortisone, hydrocortisone acetate, hydrocortisone butyrate, hydrocortison butyrate propionate, flumethasone pivalate, triamcinolone, triamcinolone acetonide, dexamethasone, dexamethasone acetate, dexamethasone valerate, dexamethasone propionate, fluocinolone, fluocinolone acetonide, betamethasone, betamethasone valerate, betamethasone dipropionate, becromethasone propionate, clobetasone butyrate, fludroxycortide, fluocinonide, flunisolide, amcinonide, difluprednate, diflucortolone valerate, diflorasone acetate, clobetasol propionate; wherein the amount of said adrenocortical hormone is about one half to about one-tenth of the usual clinical dose of said adrenocortical hormone and
   (b) from about 0.005 to about 0.1% by weight of hyaluronic acid.

2. A topical dermatological composition according to claim 1, wherein the adrenocortical hormone is hydrocortisone butyrate, hydrocortisone acetate or cortisone acetate.

3. A method of producing a topical dermatological composition, which comprises mixing an adrenocortical hormone and from about 0.005 to about 0.1% by weight of hyaluronic acid, the amount of said adrenocortical hormone being about one half to about one-tenth of the usual clinical dose of the adrenocortical hormone, with other ingredients.

4. A method according to claim 3, wherein the adrenocortical hormone is hydrocortisone butyrate, hydrocortisone acetate or cortisone acetate.

5. A method of combatting skin disease, which comprises applying a topical dermatological composition as claimed in claim 1.

6. A method according to claim 5, wherein the adrenocortical hormone is hydrocortisone butyrate, hydrocortisone acetate or cortisone acetate.

* * * * *